Figure 1:
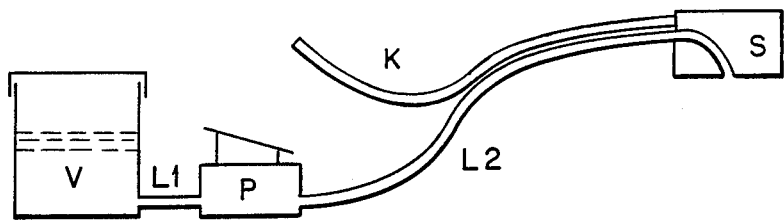

United States Patent [19]

Frass et al.

[11] Patent Number: 4,844,080

[45] Date of Patent: Jul. 4, 1989

[54] ULTRASOUND CONTACT MEDIUM DISPENSER

[76] Inventors: Michael Frass, Viechtlgasse 11; Reinhard Frenzer, both of Mödling, Austria

[21] Appl. No.: 210,131

[22] Filed: Jun. 10, 1988

Related U.S. Application Data

[63] Continuation of Ser. No. 16,539, Feb. 19, 1987, abandoned.

[51] Int. Cl.[4] .............................................. A61B 8/00
[52] U.S. Cl. ......................... 128/660.01; 128/662.03; 73/644
[58] Field of Search ...................... 128/662.06, 660.01, 128/662.03; 604/53, 140; 73/644

[56] References Cited

U.S. PATENT DOCUMENTS

| | | | |
|---|---|---|---|
| 2,971,509 | 2/1961 | Cohen | 604/140 |
| 4,252,125 | 2/1981 | Iinuma | 73/644 |
| 4,282,880 | 8/1981 | Gardineer et al. | 128/660.01 |
| 4,466,443 | 8/1984 | Utsugi | 128/662.06 |
| 4,665,925 | 5/1987 | Miller | 128/662.06 X |
| 4,697,595 | 10/1987 | Breyer et al. | 128/662.06 |
| 4,714,460 | 12/1987 | Calderon | 604/53 X |

OTHER PUBLICATIONS

Taylor, W. B. et al, "A High Resolution Transrectal UTS System", UTS in Medicine & Biology, vol. 5, No. 2, pp. 129–138, (1979).

*Primary Examiner*—Francis Jaworski
*Attorney, Agent, or Firm*—McAulay, Fisher, Nissen & Goldberg

[57] ABSTRACT

The coupling agent dispenser serves to guide and, at the same, possibly to warm up the coupling agent, which is required for many medical examinations, directly during the examination from a reservoir to a diagnostic probe.

5 Claims, 1 Drawing Sheet

ULTRASOUND CONTACT MEDIUM DISPENSER

This application is a continuation of application Ser. No. 016,539, filed 2/19/87, and now abandoned.

The invention relates to a device, by means of which the ultrasound coupling agent, required for a series of medical examinations, such as ultrasonic examinations and Doppler examinations, can be transported from a reservoir to the diagnostic probe and, at the same time, also heated if necessary.

For said examinations, an area of a diagnostic probe, for example, the so-called sound head in the case of ultrasonic examinations, is brought into contact with the anatomically specified area above the part of the body to be examined. The diagnostic probe may also be brought into contact with an inanimate object. The oscillations employed for the examination, for example, ultrasound in the megahertz range in the case of ultrasonic examinations, are incapable of negotiating the air-filled gap that occurs between the ultrasonic probe and the surface of the body. For this reason, a coupling agent, which usually is a water-containing gel but may also be a fatty oil, is applied on the surface of the body before the actual examination is carried out. This coupling agent displaces the air that hinders the examination and thus makes the examination possible.

At present, before the start of the actual examination, said coupling agent is applied by means of a plastic wash bottle or similar device on the surface of the body above the part of the body that is to be examined, after which the examination is commenced. Usually however, it proves to be necessary to interrupt the examination one or more times in order to apply coupling agent once again, since additional areas of the body, which have previously not been provided with the coupling agent, are to be examined or since the coupling agent, due to the heat of the body, has dried up in the course of the examination.

Some examining equipment has a heating chamber, in which said wash bottle is placed for some time before the examination and the coupling agent can be warmed up. Heating the contact medium is absolutely advisable since, by so doing, tension in the patient, which is produced by the coldness of the coupling agent and can hinder the examination, can be avoided. Warming up the coupling agent is, however, made much more difficult by the gel character of the coupling agent and the lack of thermal convection in the gel associated therewith, so that the heat output of the heating chamber is overtaxed if several examinations are carried out directly one after the other.

It is the object of the invention to provide a device, by means of which said coupling agent can be dispensed from a reservoir to the site of the diagnostic probe and, at the same time, perhaps heated without interrupting the examination.

This equipment comprises a reservoir for the coupling agent, a hose line from the reservoir to the site of the diagnostic probe, such as the sound head, as well as a device for conveying the coupling agent, such as a pump or a reservoir under pressure. If the coupling agent is not to be transported continuously to the site of the diagnostic probe, but on demand by activating a pump, a valve or an electrical contact, an appropriate control device has to be provided.

The coupling agent may be warmed up at a suitable location. If the warming up takes place in or near the reservoir, attention must be paid to adequate heat insulation of the hose line. The output of the warming-up device may also be controlled in a suitable manner, for example, by a thermostat or by using thermostated water.

Some companies package the coupling agent, which is produced by them, in a plastic bag for transport. This plastic bag may function, at the same time, as the above-mentioned reservoir, so that, under certain circumstances, a transfer of the coupling agent to the reservoir may be omitted.

The objective device for conveying and possible warming up the aforementioned coupling agent may be constructed as an independent piece of equipment, an addition to a piece of equipment requiring the use of coupling agents, or as a part of such a piece of equipment.

In the following, three possible embodiments of the objective device are explained by means of schematic drawings.

FIG. 1 shows a very simple version. From the reservoir V, coupling agent is conveyed through hose line L1 to the pump P, which is activated by the foot of the examiner, and from there further through the hose line L2 to the location of the diagnostic manipulation. Hose line L2 may be connected to the electric cable K and to the diagnostic probe S of the diagnostic instrument.

Figure 2:
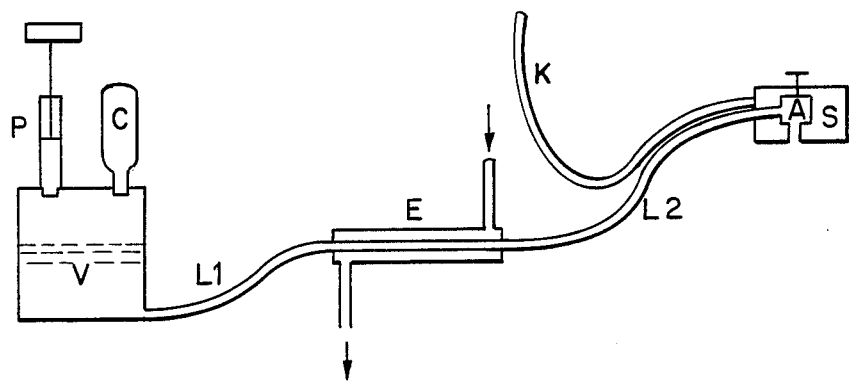

FIG. 2 shows the diagrammatic view of equipment operating with pressure. The reservoir V is placed under pressure by means of pump P or cartridge C, which is filled with compressed gas. If the valve A, disposed in the region of the diagnostic probe S, is opened, the pressure drives the coupling agent through hose lines L1 and L2 as well as through the heater E, where the coupling agent is heated by warm water according to the counter current principle.

Figure 3:
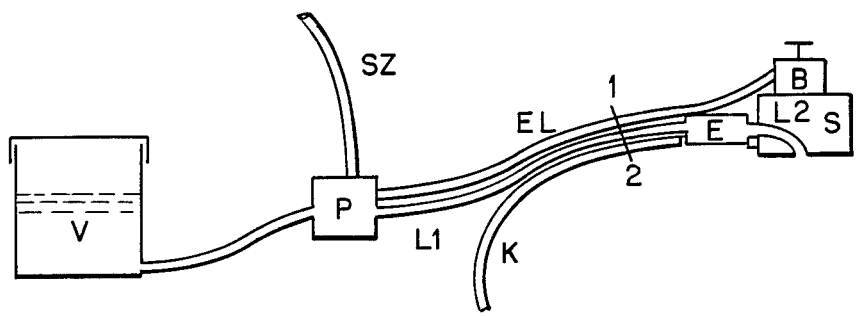

FIG. 3 shows the diagrammatic view of equipment operated with an electrically driven pump. From the reservoir V, the coupling agent is forced by means of pump P through the hose line L1, the electrically operated heater E in the region of the diagnostic probe S and through the hose line L2. The pump P is switched on and off through electrical contact B by means of the electric lead EL. Electric power is supplied to the pump P through electric lead SZ. The pump may also be driven by a parameter obtained from the diagnostic instrument, such as "image freeze".

The section 1-2 may intersect two separate electrical leads K and EL and a hose line L1; the leads and line may, however, also be combined to a uniform strand.

We claim:

1. A mechanism for transporting a coupling agent useable for various medical examination such as ultrasonic and doppler examinations, the mechanism comprising:
    a moveable probe;
    a reservoir for holding a coupling agent;
    a flexible hose having an inlet end adapted to be placed in communication with said reservoir and an outlet end in communication with said probe;
    pumping means coupled to said reservoir and to said probe to pump coupling agent from said reservoir through said flexible hose to said probe for application to a patient;
    control means adapted to work with said pumping means, said control means being positioned in said moveable probe, said control means for controlling the flow of coupling agent from said reservoir to said probe;

said pumping means providing transport of said coupling agent in solely one direction, from said reservoir to said probe;

flexible electrical cable means coupled to said probe, said flexible electrical cable means for providing information signals relevant to the examination; and said flexible hose and said flexible electrical cable means being the sole physical constraint on movement on said moveable probe.

2. The mechanism of claim 1 and further including a heater at said flexible hose for heating said coupling agent as it passes through said flexible hose from said reservoir to said probe.

3. The mechanism of claim 1 wherein said control means is a valve capable of assuming an open state in which coupling agent flows through said hose from said reservoir to said probe or a closed state in which said coupling agent does not so flow.

4. The mechanism of claim 3 wherein said control means is a valve capable of assuming an open state in which coupling agent flows through said hose from said reservoir to said probe or a closed state in which said coupling agent does not so flow.

5. The mechanism of claim 1 wherein said pumping means includes a cartridge filled with compressed gas to pressurize said reservoir, said cartridge being in communication with said reservoir.

* * * * *